United States Patent
Brannan et al.

(10) Patent No.: US 9,901,398 B2
(45) Date of Patent: Feb. 27, 2018

(54) MICROWAVE ANTENNA PROBES

(71) Applicant: COVIDIEN LP, Mansfield, MA (US)

(72) Inventors: Joseph D. Brannan, Erie, CO (US);
William O. Reid, Jr., Frederick, CO (US); Darion R. Peterson, Boulder, CO (US); Kaylen J. Haley, Westminster, CO (US); Richard A. Willyard, Longmont, CO (US); Kenlyn S. Bonn, Lakewood, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/908,463

(22) Filed: Jun. 3, 2013

(65) Prior Publication Data
US 2014/0005657 A1 Jan. 2, 2014

Related U.S. Application Data

(60) Provisional application No. 61/666,095, filed on Jun. 29, 2012.

(51) Int. Cl.
*A61B 18/18* (2006.01)
*A61B 18/00* (2006.01)

(52) U.S. Cl.
CPC *A61B 18/1815* (2013.01); *A61B 2018/00023* (2013.01); *A61B 2018/1861* (2013.01); *A61B 2018/1869* (2013.01)

(58) Field of Classification Search
CPC ...... A61B 18/1815; A61B 2018/00202; A61B 2018/0091; A61B 2018/00946;
(Continued)

(56) References Cited

U.S. PATENT DOCUMENTS

D223,367 S 4/1972 Kountz
4,139,005 A * 2/1979 Dickey .......................... 138/89
(Continued)

FOREIGN PATENT DOCUMENTS

CN 1103807 A 6/1995
DE 390937 C 3/1924
(Continued)

OTHER PUBLICATIONS

U.S. Appl. No. 13/419,981, filed Mar. 14, 2012, Joseph D. Brannan.
(Continued)

*Primary Examiner* — Jaymi Della
*Assistant Examiner* — Eunhwa Kim

(57) ABSTRACT

A surgical probe includes a connection hub, an antenna assembly, and an outer jacket. The antenna assembly is coupled to the connection hub, extends distally from the connection hub, and includes a radiating portion coupled thereto at the distal end thereof. The radiating portion is configured to deliver energy to tissue to treat tissue. The outer jacket is coupled to the connection hub, extends distally therefrom, and is disposed about the radiating portion. The outer jacket includes a distal end member configured to be spaced-apart from the radiating portion a target axial distance. One or more of the couplings between the antenna assembly and the connection hub, the radiating portion and the antenna assembly, and the outer jacket and the connection hub defines a flexible configuration permitting axial movement therebetween to maintain the target axial distance between the radiating portion and the distal end member.

19 Claims, 12 Drawing Sheets

(58) Field of Classification Search
CPC .............................. A61B 2018/00952; A61B
2018/1823–2018/1892; A61B 18/18;
A61B 18/1487
USPC .......................................................... 606/33
See application file for complete search history.

(56) References Cited

U.S. PATENT DOCUMENTS

| | | |
|---|---|---|
| D263,020 S | 2/1982 | Rau, III |
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| D354,218 S | 1/1995 | Van De Peer |
| D424,693 S | 5/2000 | Pruter |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| 6,427,089 B1 | 7/2002 | Knowlton |
| 6,506,189 B1 | 1/2003 | Rittman, III et al. |
| 6,508,775 B2* | 1/2003 | McKenzie et al. ............... 601/2 |
| 6,652,520 B2 | 11/2003 | Moorman et al. |
| D487,039 S | 2/2004 | Webster et al. |
| 6,702,803 B2* | 3/2004 | Kupperblatt et al. ..... 604/890.1 |
| D496,997 S | 10/2004 | Dycus et al. |
| D499,181 S | 11/2004 | Dycus et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| 7,160,292 B2 | 1/2007 | Moorman et al. |
| D541,418 S | 4/2007 | Schechter et al. |
| D541,938 S | 5/2007 | Kerr et al. |
| 7,276,061 B2 | 10/2007 | Schaer et al. |
| D564,662 S | 3/2008 | Moses et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 8,059,059 B2 | 11/2011 | Bonn |
| 8,069,553 B2 | 12/2011 | Bonn |
| 8,118,808 B2 | 2/2012 | Smith et al. |
| 8,226,653 B2* | 7/2012 | Blackwell et al. ............. 606/71 |
| 8,361,062 B2 | 1/2013 | Bonn |
| D681,810 S | 5/2013 | DeCarlo |
| 8,469,953 B2* | 6/2013 | DeCarlo ......................... 606/41 |
| 2001/0008966 A1* | 7/2001 | Arndt et al. ..................... 606/33 |
| 2005/0245919 A1* | 11/2005 | van der Welde .. A61B 18/1815 606/33 |
| 2006/0095027 A1 | 5/2006 | Eggers |
| 2007/0088354 A1* | 4/2007 | Sugita .............................. 606/46 |
| 2007/0203551 A1 | 8/2007 | Cronin et al. |
| 2008/0033422 A1* | 2/2008 | Turner et al. ..................... 606/33 |
| 2008/0269558 A1 | 10/2008 | Yahagi et al. |
| 2009/0131926 A1* | 5/2009 | Rusin et al. ..................... 606/33 |
| 2009/0187180 A1* | 7/2009 | Brannan ......................... 606/33 |
| 2009/0222002 A1* | 9/2009 | Bonn ...................... A61B 18/18 606/33 |
| 2009/0291490 A1* | 11/2009 | Spradling ................... 435/292.1 |
| 2009/0295674 A1 | 12/2009 | Bonn |
| 2011/0054459 A1 | 3/2011 | Peterson |
| 2011/0056069 A1 | 3/2011 | Bonn |
| 2011/0118720 A1 | 5/2011 | Turner et al. |
| 2011/0118724 A1 | 5/2011 | Turner et al. |
| 2011/0213362 A1 | 9/2011 | Lee et al. |
| 2011/0238054 A1 | 9/2011 | Kim et al. |
| 2011/0238055 A1* | 9/2011 | Kim et al. ....................... 606/33 |
| 2011/0295245 A1* | 12/2011 | Willyard et al. ............... 606/33 |
| 2012/0042506 A1 | 2/2012 | Bonn |
| 2012/0110834 A1 | 5/2012 | Smith et al. |
| 2012/0161786 A1 | 6/2012 | Brannan |
| 2012/0172862 A1 | 7/2012 | Brannan |
| 2012/0172863 A1 | 7/2012 | Brannan |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1 159 926 A2 | 12/2001 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |

(56) References Cited

FOREIGN PATENT DOCUMENTS

| | | | |
|---|---|---|---|
| JP | 2001003776 A | 1/2001 | |
| JP | 2001008944 A | 1/2001 | |
| JP | 2001029356 A | 2/2001 | |
| JP | 2001037775 A | 2/2001 | |
| JP | 2001128990 A | 5/2001 | |
| JP | 2001231870 A | 8/2001 | |
| JP | 2008142467 A | 6/2008 | |
| JP | 2010110579 A | 5/2010 | |
| KR | 20070093068 A | 9/2007 | |
| KR | 20100014406 A | 2/2010 | |
| KR | 20120055063 A | 5/2012 | |
| SU | 166452 | 11/1964 | |
| SU | 401367 A1 | 10/1973 | |
| SU | 727201 A2 | 4/1980 | |
| WO | 00/36985 A2 | 6/2000 | |
| WO | 20101035831 A1 | 4/2010 | |

OTHER PUBLICATIONS

U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Joseph D. Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011.414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
LigaSureTM Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.

(56) References Cited

OTHER PUBLICATIONS

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-"COA-COMP"" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098; Oct. 14, 1993; Roger A. Stern.
U.S. Appl. No. 08/483,742; Jun. 7, 1995; Roger A. Stern.
International Search Report from corresponding PCT/US2013/044774 dated Nov. 4, 2013.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM " Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. Mi, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.

(56) References Cited

OTHER PUBLICATIONS

Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, VOL., BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression.Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
Partial Supplementary European search report issued in corresponding application No. 13809290.3 dated Feb. 2, 2016.
Chinese Office Action issued in corresponding application No. 201380034565.5 dated Jan. 17, 2017.
Australian office action issued in corresponding application No. 2013280972 dated Jan. 19, 2017.
Extended European search report issued in corresponding application No. 13809290.3 dated Jun. 9, 2016.
Japanese Office Action and English language translation from Appl. No. JP 2015-52023 dated Mar. 22, 2017.
Japanese Office Action and English language translation issued in Appl. No. JP 2015-520230 dated Jul. 3, 2017.
Australian Examination report No. 2 issued in Appl. No. Au 2013280972 dated Jul. 26, 2017.
Chinese Office Action and English translation issued in application No. CN 201380034565.5 dated Jun. 23, 2017.

* cited by examiner

MICROWAVE ANTENNA PROBES

CROSS REFERENCE TO RELATED APPLICATION

The present application claims the benefit of and priority to U.S. Provisional Application Ser. No. 61/666,095, filed on Jun. 29, 2012, the entire contents of which are incorporated herein by reference.

BACKGROUND

Technical Field

The present disclosure relates to surgical instruments and, more particularly, to microwave antenna probes for applying energy, e.g., microwave energy, to tissue to treat tissue, e.g., ablate tissue.

Background of Related Art

Treatment of certain diseases requires destruction of malignant tissue growths, e.g., tumors. It is known that tumor cells denature at elevated temperatures that are slightly lower than temperatures injurious to surrounding healthy cells. Known treatment methods, such as hyperthermia therapy, are utilized to heat tumor cells above the temperature necessary to destroy the tumor cells, while maintaining adjacent healthy cells at lower temperatures to avoid irreversible damage to the surrounding healthy cells. Such methods typically involve applying electromagnetic radiation to heat tissue, e.g., to ablate and/or coagulate tissue. In particular, microwave energy is used to ablate and/or coagulate tissue to denature or kill cancerous cells. There are several types of microwave antenna probes, e.g., monopole probes and dipole probes, that are currently used to radiate microwave energy generally perpendicularly from the axis of the probe to treat adjacent tissue.

SUMMARY

As used herein, the term "distal" refers to the portion that is being described which is further from a user, while the term "proximal" refers to the portion that is being described which is closer to a user. Further, to the extent they are consistent with one another, any of the aspects described herein may be used in conjunction with any of the other aspects described herein.

In accordance with aspects of the present disclosure, a surgical probe is provided generally including a connection hub, an antenna assembly, and an outer jacket. The antenna assembly is coupled to the connection hub and extends distally from the connection hub. A radiating portion is coupled to the antenna assembly at the distal end of the antenna assembly. The radiating portion is configured to deliver energy to tissue to treat tissue. The outer jacket is coupled to the connection hub and also extends distally from the connection hub. The outer jacket is disposed about the radiating portion and including a distal end member configured to be spaced-apart from the radiating portion a target axial distance. One or more of the coupling between the antenna assembly and the connection hub, the coupling between the radiating portion and the antenna assembly, and the coupling between the outer jacket and the connection hub defines a flexible configuration permitting axial movement therebetween to maintain the target axial distance between the radiating portion and the distal end member.

In one aspect, the radiating portion is coupled to the antenna assembly via a flexible conductive joint configured to electrically couple the radiating portion and the antenna assembly to one another and to permit relative axial movement of the radiating portion with respect to the antenna assembly.

In another aspect, a spacer is interdisposed between the distal end member and the radiating portion. The spacer is configured to flex the one or more flexible couplings to maintain the target axial distance between the radiating portion and the distal end member. The spacer may be formed from a substantially rigid material, a compressible material, or an expandable material. Further, the spacer may be formed from a dissolvable material.

In another aspect, fluid is configured to be circulated within the connection hub and the outer jacket at a predetermined pressure to flex the one or more flexible couplings to maintain the target axial distance between the radiating portion and the distal end member. In such an aspect, a pressure sensor configured to sense the fluid pressure within the connection hub and the outer jacket may also be provided.

In still another aspect, the antenna assembly includes a transition sealingly coupled to the connection hub via a flexible coupling. The flexible coupling allows the antenna assembly to be axially movable relative to the connection hub. Further, a clip may be provided for engagement about the connection hub to inhibit axial movement of the antenna assembly relative to the connection hub.

In yet another aspect, the outer jacket includes a ferrule sealingly coupled to the connection hub via a flexible coupling. The flexible coupling allows the outer jacket to be axially movable relative to the connection hub. Further, a clip may be provided for engagement about the connection hub to inhibit axial movement of the outer jacket relative to the connection hub.

In still yet another aspect, the distal end member includes a trocar configured to facilitate penetration through tissue.

In accordance with aspects of the present disclosure, a surgical probe is provided generally including an antenna assembly, an outer jacket, and a phase-change material. The antenna assembly defines a radiating portion configured to deliver energy to tissue to treat tissue. The outer jacket is disposed about the radiating portion and includes a distal end member configured to be spaced-apart from the radiating portion a target axial distance. The phase-change material is disposed within the outer jacket and substantially surrounds the radiating portion. The phase-change material is transitionable, upon activation of the antenna assembly, between a solid state, for maintaining the target axial distance between the distal end member and the radiating portion, and a fluid state, for absorbing heat to maintain the antenna assembly in a relatively cooled state during use.

In one aspect, the energy delivered from the radiating portion to tissue effects heating of the phase-change material such that the phase-change material is transitioned from the solid state to the fluid state.

In another aspect, the distal end member includes a trocar configured to facilitate penetration through tissue.

Another surgical probe provided in accordance with aspects of the present disclosure generally includes a connection hub, an antenna assembly, and an outer jacket. The antenna assembly extends distally from the connection hub and includes a radiating portion coupled thereto at the distal end of the antenna assembly. The radiating portion is configured to deliver energy to tissue to treat tissue. The outer jacket likewise extends distally from the connection hub and is disposed about the radiating portion. The outer jacket includes a distal end member and a ferrule engaged thereto. The ferrule is operably coupled to the connection hub and is axially movable relative to the connection hub to axially translate the distal end member relative to the radiating portion to achieve a target axial spacing therebetween.

In one aspect, rotation of the ferrule relative to the connection hub effects axial translation of the distal end member relative to the radiating portion.

In another aspect, the ferrule includes a threaded annular flange configured to operably engage complementary threading of the connection hub such that rotation of the ferrule relative to the connection hub effects axial translation of the distal end member relative to the radiating portion.

In another aspect, the ferrule further includes a base configured for insertion into the connection hub to sealingly engage the ferrule within the connection hub.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
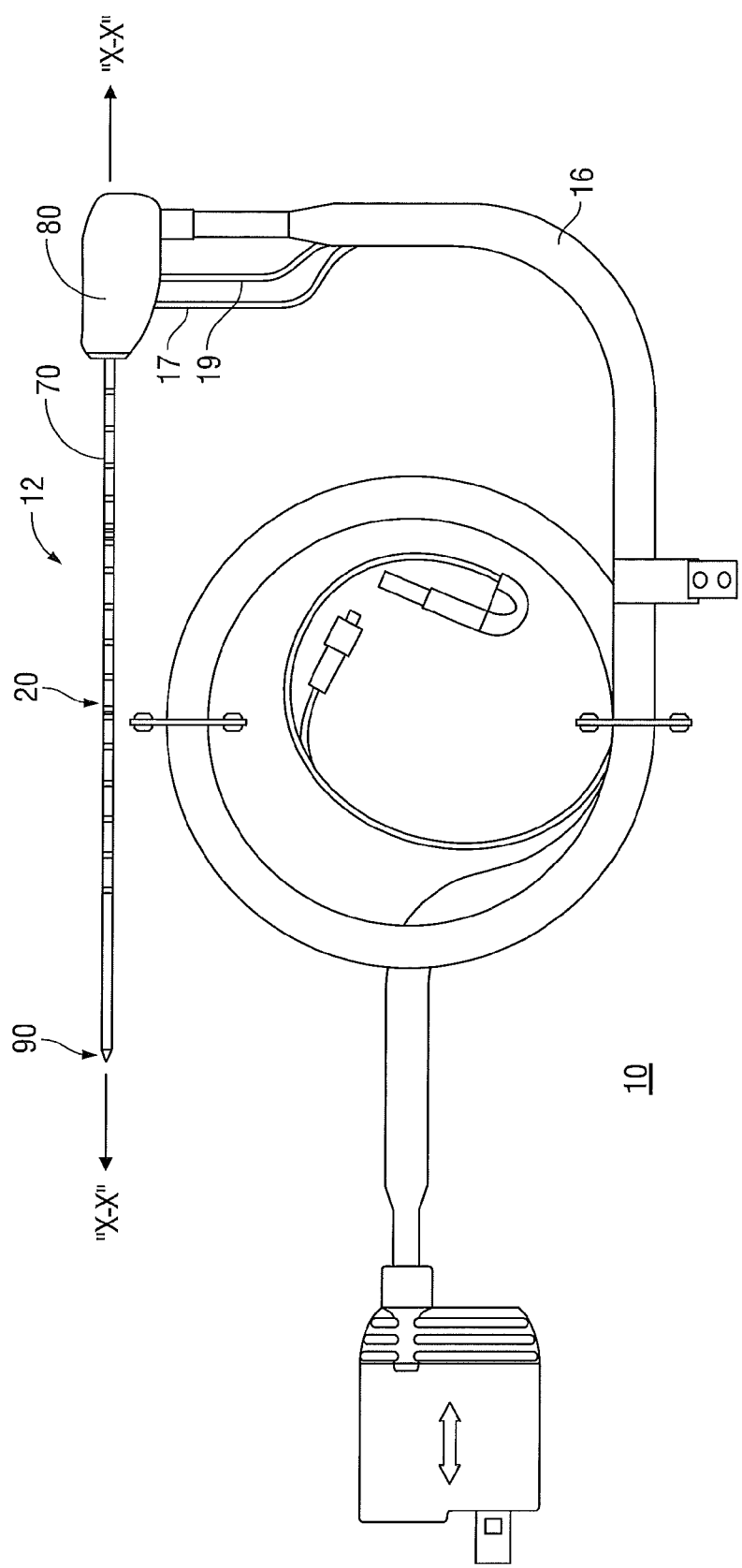
FIG. 1 is a side view of a microwave ablation system provided in accordance with the present disclosure.
Figure 2:
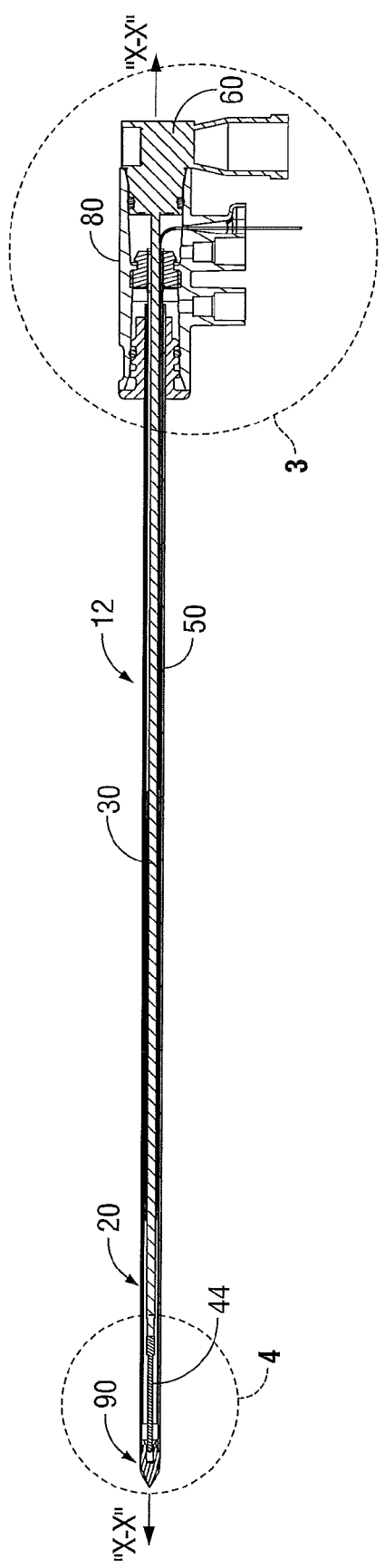
FIG. 2 is a longitudinal, cross-sectional view of a microwave antenna probe of the microwave ablation system of FIG. 1.

It has been found that, with respect to surgical instruments configured to apply energy to tissue to treat tissue, proper spacing between the energy radiating portion or portions and the other components of the instrument helps facilitate optimal performance of the instrument. With respect to microwave ablation probes in particular, it has been found that proper axial spacing between the distal end of the radiating portion of the antenna assembly and the proximal surface of the base of the trocar helps ensure optimal performance of the microwave antenna probe. More specifically, if the axial distance between the distal end of the radiating portion and the proximal surface of the trocar is too large, the ablation zone (ablation shape) may be sub-optimal and complete ablation of tissue may not be readily achieved. Likewise, where the axial distance between the distal end of the radiating portion and the proximal surface of the trocar is too small, ablation performance may be degraded. Accordingly, maintaining optimal axial spacing, e.g., the target axial distance, between the radiating portion and the trocar during use helps facilitate optimal performance.

The optimal axial spacing, e.g., the target axial distance, between the radiating portion and the trocar may depend on the dimensions and configuration of the microwave antenna probe, and may be determined empirically, experimentally, or in any other suitable fashion. Variation in the axial distance from probe to probe may arise from inconsistent lengths or sizes of the individual components, variation in the engagements between or positions of the various components relative to one another, inconsistencies in assembly (particularly with respect to user-assembled devices), and/or other factors. The various embodiments of probes described in detail hereinbelow are configured to overcome some or all of these factors that contribute to variation in axial distance, thereby maintaining the target axial distance during use and, thus, facilitating optimal performance of the probe.

Turning now to FIGS. 1-7, a microwave ablation system provided in accordance with the present disclosure is shown generally identified by reference numeral 10. Microwave ablation system 10 includes a microwave antenna probe 12 configured to couple to a microwave generator (not shown) via a flexible coaxial cable 16. Although the present disclosure is shown and described with reference to microwave antenna probes, the present disclosure is equally applicable for use in determining and/or setting a particular distance between components of any suitable energy-based surgical instrument. For the purposes herein, microwave antenna probe 12 is generally described.

With continued reference to FIGS. 1-7, microwave antenna probe 12 generally includes an antenna assembly 20, an outer jacket and trocar assembly 70, and a connection hub 80. Antenna assembly 20 defines a longitudinal axis "X-X" and includes a radiating section that defines a dipole configuration, e.g., the radiating section includes a feed gap 43 and proximal and distal radiating portions 42, 44. A feedline 30 extends proximally from the radiating section into connection hub 80, ultimately coupling to cable 16 via transition 60 to connect antenna assembly 20 to the generator (not shown) for supplying energy thereto. Feedline 30 defines a coaxial configuration having an inner conductor 32 surrounded by an insulator 34. Insulator 34, in turn, is surrounded by an outer conductor 36, thus defining the coaxial configuration of feedline 30. Feedline 30 may be formed from a semi-rigid or flexible coaxial cable, although other configurations are also contemplated.

Figure 7:
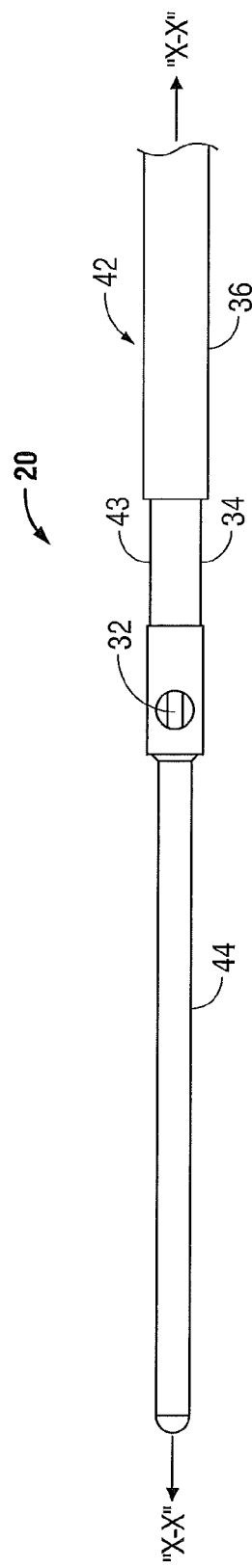
FIG. 7 is an enlarged view of the area of detail indicated as "7" in FIG. 6.

As mentioned above, and with reference to FIGS. 2, 4, and 6-7, the radiating section of antenna assembly 20 includes feed gap 43, proximal radiating portion 42, and distal radiating portion 44. Feed gap 43 is defined by the portion of inner conductor 32 and insulator 34 of feedline 30 that extends distally from outer conductor 36, e.g., outer conductor 36 may be stripped from the distal end of coaxial feedline 30 to define feed gap 43. Proximal radiating portion 42 is defined by the portion of feedline 30 disposed between the proximal end of feed gap 43 and the distal end of the choke 50. Distal radiating portion 44 is attached to feed gap 43 via any suitable process and extends distally therefrom. For example, as shown in FIG. 7, distal radiating portion 44 may be soldered to inner conductor 32 of feed gap 43 to establish electromechanical contact therebetween.

Antenna assembly 20, as shown in FIGS. 2, 4, and 6-7, further includes a choke or balun 50 disposed about feedline 30. Choke 50 includes an inner dielectric layer and an outer conductive layer. Choke 50 may be a quarter-wavelength shorted choke that is shorted to outer conductor 36 of feedline 30 at the proximal end of choke 50, although other configurations are contemplated. The dielectric layer of choke 50 may also be configured to extend distally beyond the conductor layer thereof towards the distal end of antenna assembly 20.

Figure 3:
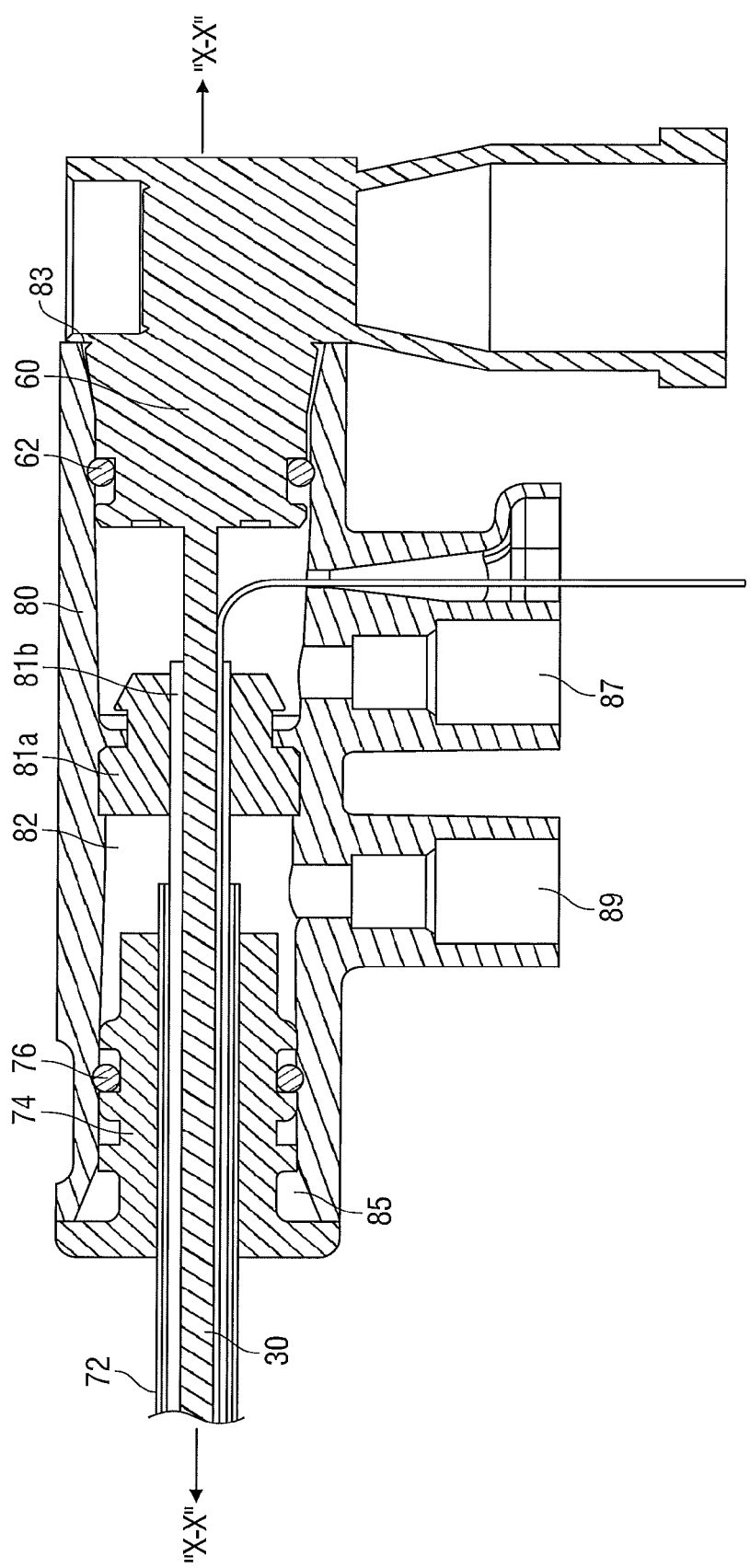
FIG. 3 is an enlarged view of the area of detail indicated as "3" in FIG. 2.
Figure 4:
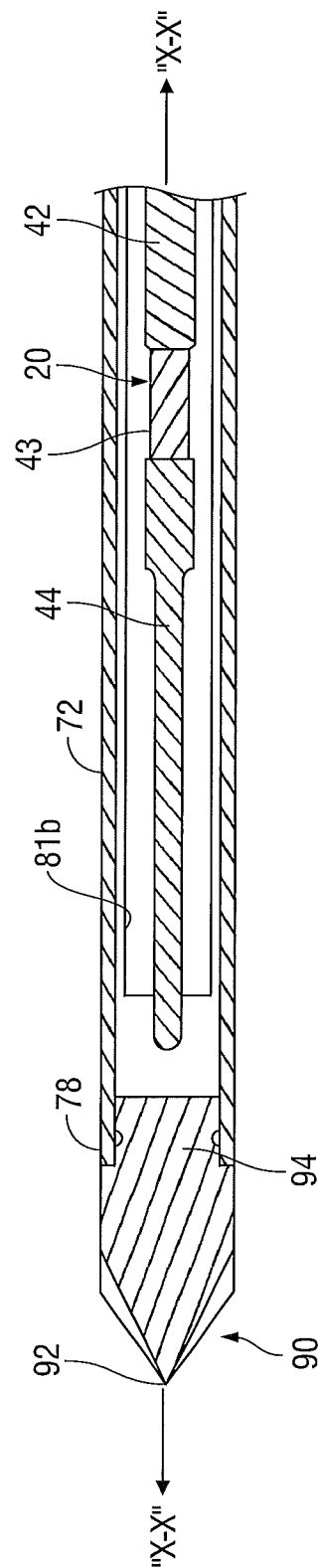
FIG. 4 is an enlarged view of the area of detail indicated as "4" in FIG. 2.
Figure 5:
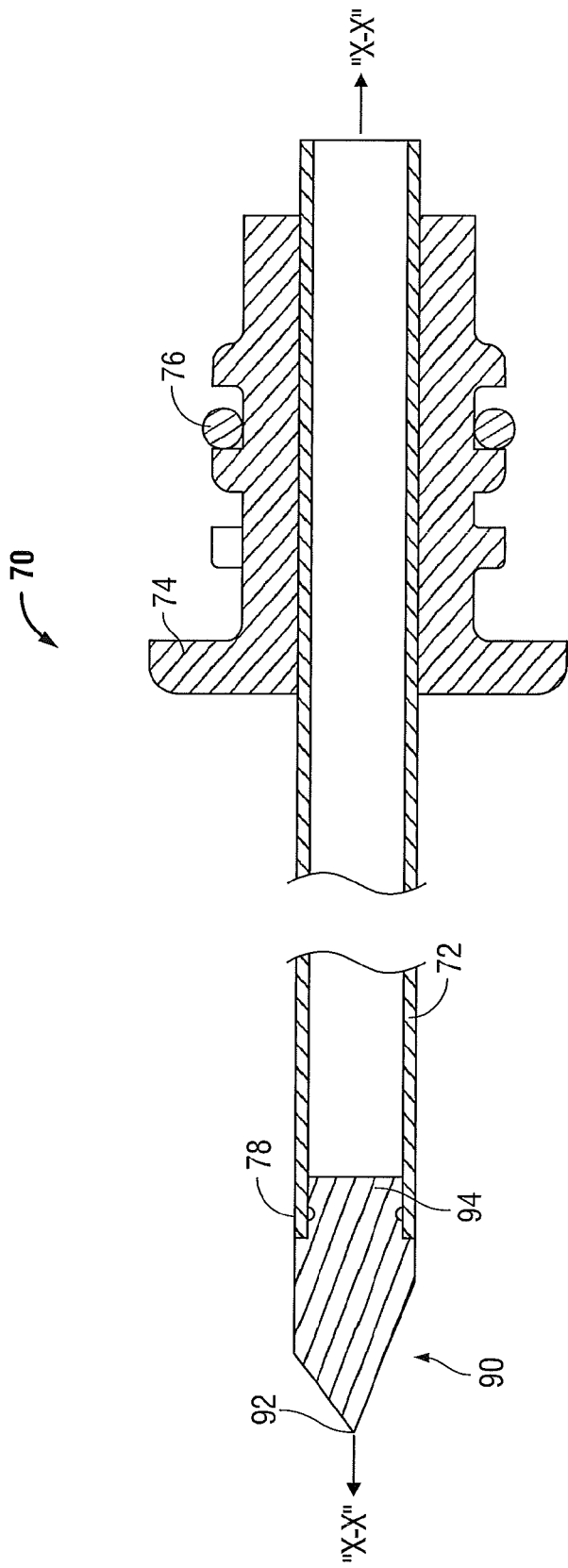
FIG. 5 is a longitudinal, cross-sectional view of an outer jacket and trocar assembly of the microwave antenna probe of FIG. 2.
Figure 6:
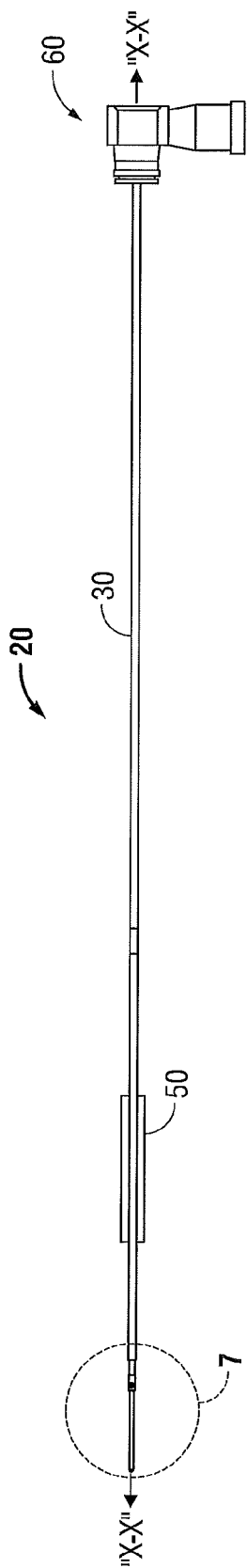
FIG. 6 is a side view of an antenna assembly of the microwave antenna probe of FIG. 2.

With additional reference to FIG. 3, as mentioned above, antenna assembly 20 includes a transition 60 from which feedline 30 extends. Feedline 30 extends into transition 60, wherein inner conductor 32 is coupled to an inner conductor (not explicitly shown) of coaxial cable 16 and outer conductor 36 is coupled to an outer conductor (not explicitly shown) of coaxial cable 16, while maintaining the spacing therebetween via an insulator (not explicitly shown). Cable 16 may be secured to feedline 30 within transition 60 via soldering, laser welding, or any other suitable process for establishing electromechanical contact therebetween. Transition 60 is disposed within proximal port 83 of connection hub 80 and is sealingly engaged therein via O-ring 62. More specifically, during assembly, the radiating section and feedline 30 of antenna assembly 20 are inserted through proximal port 83 and lumen 82 of connection hub 80 such that transition 60 may ultimately be inserted into proximal port 83 of connection hub 80 to sealingly engage transition 60 within proximal port 83 of connection hub 80 via O-ring 62. Antenna assembly 20 may be engaged within connection hub 80 during manufacturing, or may be assembled by the user.

Outer jacket and trocar assembly 70, as best shown in FIGS. 1-5, includes an outer jacket 72 configured to surround antenna assembly 20, e.g., proximal and distal radiating portions 42, 44, feed gap 43, and feedline 30, such that a coolant fluid may be circulated thereabout to maintain antenna assembly 20 in a relatively cooled state during use. A ferrule 74 is molded or otherwise engaged about outer jacket 72 towards the proximal end thereof to facilitate sealing engagement of the proximal end of outer jacket 72 within distal port 85 of connection hub 80 via O-ring 76. That is, during assembly, ferrule 74 and, thus, the proximal end of outer jacket 72, are inserted proximally into distal port 85 of connection hub 80 sufficiently such that ferrule 74 is sealingly engaged within connection hub 80 via O-ring 76. Similarly as above, outer jacket and trocar assembly 70 may be engaged within connection hub 80 during manufacturing, or may be assembled by the user.

Outer jacket and trocar assembly 70 further includes a trocar 90 defining a tapered distal end that terminates at a pointed distal tip 92 to facilitate insertion of microwave antenna probe 12 into tissue with minimal resistance, although other configurations may also be provided. Trocar 90 may be formed from a variety of heat-resistant materials suitable for penetrating tissue, e.g., metals (stainless steel, for example), various thermoplastic materials (such as polytherimide, polyamide thermoplastic resins, etc.), or any other suitable material. Base 94 of trocar 90 is sealingly engaged within open distal end 78 of outer jacket 72 via any suitable process, e.g., using adhesives or via soldering. As such, trocar 90 sealingly encloses antenna assembly 20 within outer jacket 72 and connection hub 80.

Figure 12:
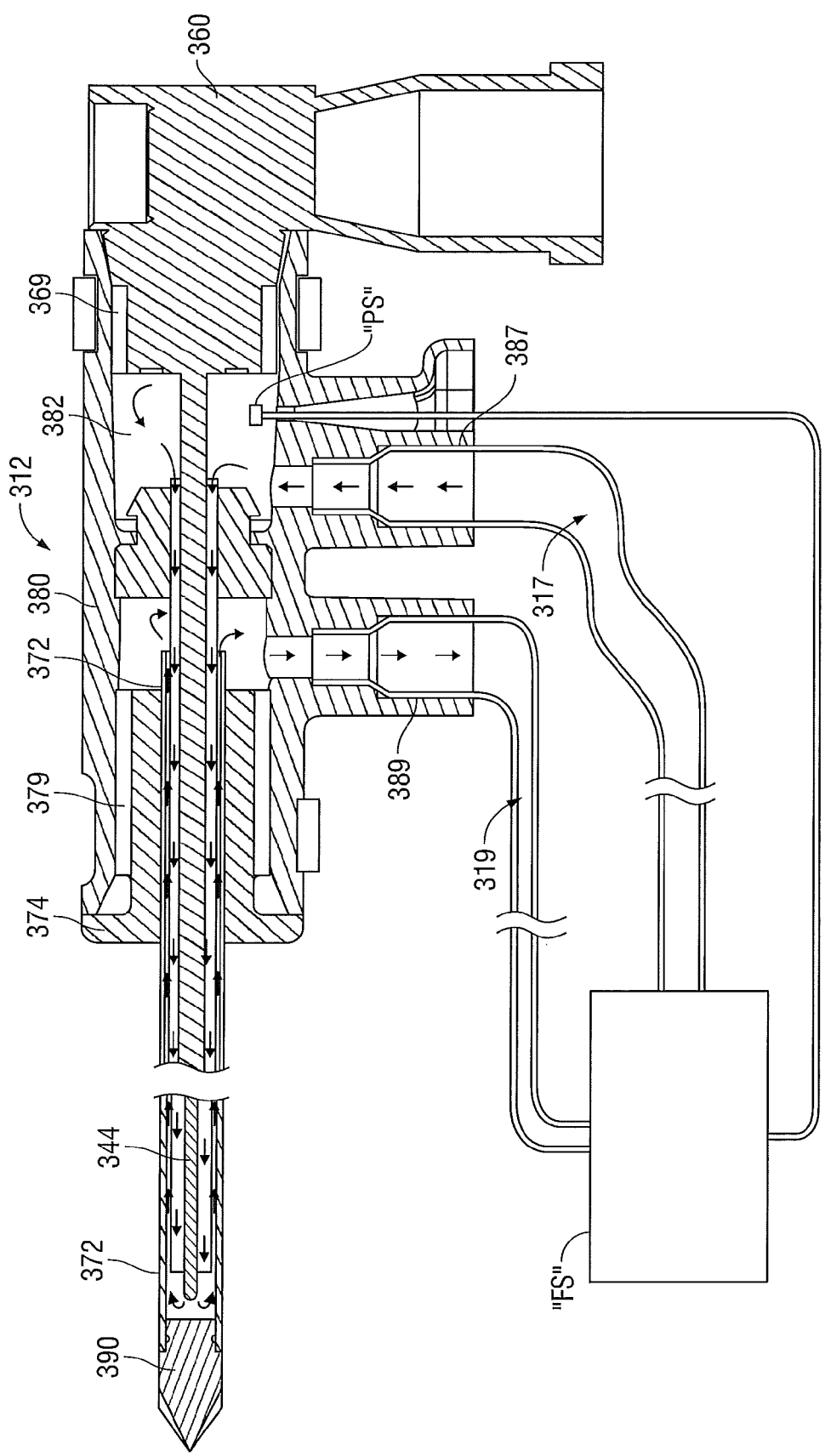
FIG. 12 is a longitudinal, cross-sectional view of another microwave antenna probe provided in accordance with the present disclosure.

Referring still to FIGS. 1-5, connection hub 80, as mentioned above, defines a longitudinal lumen 82 that is configured to receive feedline 30 therethrough, while sealingly engaging outer jacket 72 within distal port 85 and transition 60 within proximal port 83. Connection hub 80 further includes an inlet fluid port 87 and an outlet fluid port 89 that are disposed in fluid communication with lumen 82. Inlet and outlet ports 87, 89 are configured to receive tubes 17, 19 (see FIG. 1), respectively, such that coolant fluid from a coolant fluid supply "FS" (FIG. 12) be circulated through connection hub 80 and outer jacket 72. More specifically, an elastomeric (or otherwise configured) hub divider 81a is sealingly engaged within lumen 82 of connection hub 80 to isolate the inlet and outlet portions of lumen 82 of connection hub 80 from one another. Further, an inflow tube 81b is coupled to hub divider 81a and extends distally through outer jacket 72. As such, coolant fluid may flow from coolant fluid source "FS" (FIG. 12), through tube 17 and inlet port 87, into the inlet portion of lumen 82, and distally through inflow tube 81b, ultimately returning proximally through outer jacket 72 (exteriorly of inflow tube 81b), the outlet portion of lumen 82, outlet port 89, tube 19, and, ultimately, to coolant fluid source "FS" (FIG. 12). This configuration allows for the circulation of coolant fluid about antenna assembly 20 to maintain antenna assembly 20 in a relatively cooled state during use. The coolant fluid may be a liquid, gas, other flowable material, or combination thereof.

Various embodiments of microwave antenna probes configured to maintain the target axial distance between the distal radiating portion and the trocar during use, thus facilitating optimal performance of the probe, are described in detail hereinbelow. The microwave antenna probes described below are similar to microwave antenna probe 12 (FIGS. 1-7) and, thus, only the differences therebetween will be described in detail, while similarities will only be summarily described or omitted entirely.

Figure 8:
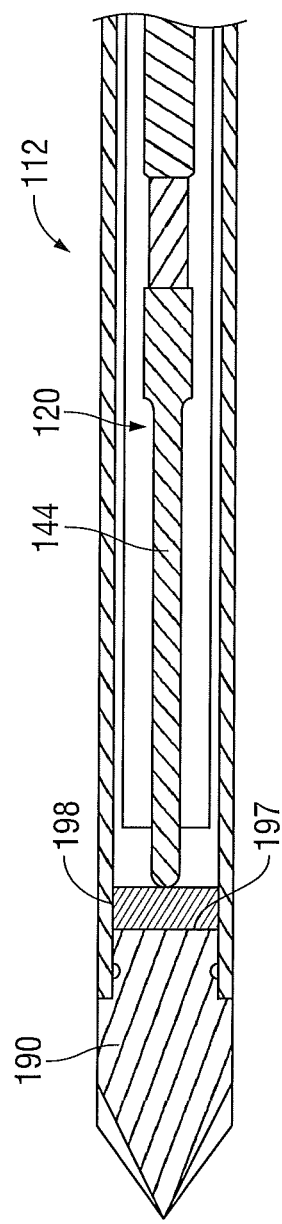
FIG. 8 is a longitudinal, cross-sectional view of a distal end of another microwave antenna probe provided in accordance with the present disclosure.
Figure 9A:
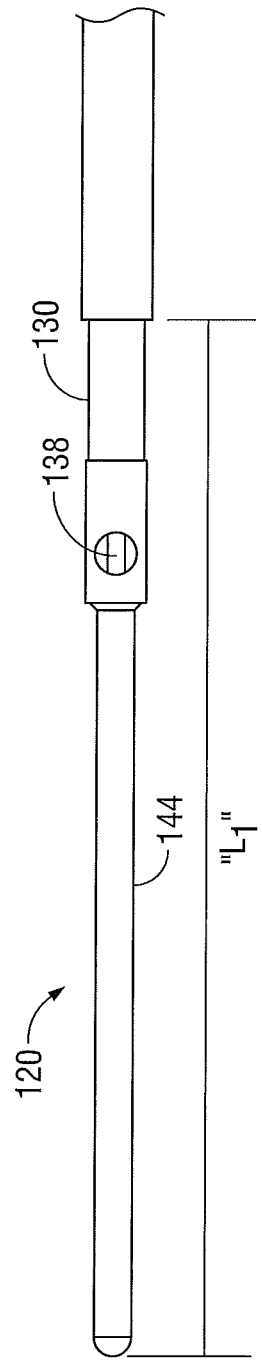
FIG. 9A is a side view of an antenna assembly provided in accordance with the present disclosure, wherein the antenna assembly is disposed in an extended condition.
Figure 9B:
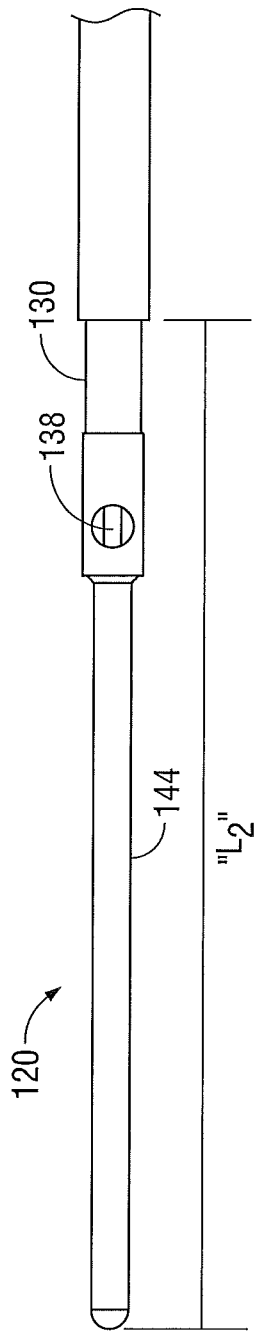
FIG. 9B is a side view of the antenna assembly of FIG. 9A, wherein the antenna assembly is disposed in a compressed condition.

Referring to FIGS. 8 and 9A-9B, another embodiment of a microwave antenna probe provided in accordance with the present disclosure and configured to maintain the target axial distance between the distal radiating portion and the trocar during use is shown generally identified by reference numeral 112. Microwave antenna probe 112 generally includes a spacer 198 disposed on proximal surface 197 of trocar 190 between trocar 190 and distal radiating portion 144. Spacer 198 may be formed from a substantially rigid material or, alternatively, may be formed from a compressible material. In embodiments wherein spacer 198 is formed from a substantially rigid material, spacer 198 is configured to define a thickness equal to the target axial distance between proximal surface 197 of trocar 190 and the distal end of distal radiating portion 144. In such embodiments, as will be described in greater detail below, distal radiating portion 144 is maintained in contact with the proximal surface of spacer 198 such that the target axial distance (equal to the thickness of spacer 198) is maintained between proximal surface 197 of trocar 190 and the distal end of distal radiating portion 144. In embodiments where spacer 198 is formed from a flexible or compressible material, spacer 198 is configured to define a thickness that is equal to or greater than the target axial distance between proximal surface 197 of trocar 190 and the distal end of distal radiating portion 144. Further, in such embodiments, spacer 198 defines a pre-determined or known compressibility.

Microwave antenna probe 112 further includes, as shown in FIGS. 9A-9B, in conjunction with FIG. 8, a flexible conductive joint 138 interconnecting distal radiating portion 144 and feedline 130 to electrically couple distal radiating portion 144 to the generator (not shown), while also permitting distal radiating portion 144 to axially translate relative to the other components of antenna assembly 120 and trocar 190 via the flexion of flexible conductive joint 138. Flexible conductive joint 138 is biased towards an extended position, e.g., the position shown in FIG. 9A, wherein the distal portion of antenna assembly 120 defines a first length "$L_1$." It is envisioned that first length "$L_1$" is greater than the fully-assembled length of the distal portion of antenna assembly 120 such, as will be described in greater detail below, flexible conductive joint 138 is at least partially flexed in the fully assembled condition of microwave antenna probe 112. Flexible conductive joint 138 is compressible from this initial, biased position to shorten the length of the distal portion of antenna assembly 120, e.g., to a length "$L_2$," as shown in FIG. 9B. As a result of this configuration, distal radiating portion 144 defines a "floating" configuration wherein distal radiating portion 144 may be axially displaced relative to trocar 190 and the other components of antenna assembly 120 via flexion, e.g., compression, of flexible conductive joint 138. Further, in embodiments where spacer 198 defines a compressible configuration, it is envisioned that flexible conductive joint 138 define a known compressibility, e.g., a compressibility equal to or proportional to that of spacer 198. Additionally or alternatively, other flexible joints (not explicitly shown) may be disposed along feedline 130 for similar purposes as flexible conductive joint 138.

With continued reference to FIGS. 8 and 9A-9B, in use, spacer 198 and the "floating" distal radiating portion 144 cooperate to maintain the target axial distance between trocar 190 and distal radiating portion 144. More specifically, in use, the distal portion of antenna assembly 120 initially defines a first length "$L_1$." In embodiments where spacer 198 defines a substantially rigid configuration having a thickness equal to the target axial distance, and upon assembly of microwave antenna probe 112, the distal end of distal radiating portion 144 contacts spacer 198, which urges distal radiating portion 144 proximally relative to trocar 190 and the other components of antenna assembly 120, thus flexing flexible conductive joint 138 and shortening the axial length of the distal portion of antenna assembly 120 to length "$L_2$." The bias of flexible conductive joint 138 maintains distal radiating portion 144 in contact with spacer 198, thus maintain the target axial distance therebetween. The degree to which the axial length of the distal portion of antenna assembly 120 is shortened, e.g., the degree to which flexible conductive joint 138 is flexed or compressed, depends on the dimensions and configuration of the components of microwave antenna probe 112, thus accounting for variation in the components and engagements therebetween.

With respect to embodiments where spacer 198 defines a compressible configuration, upon assembly of microwave antenna probe 112, the distal end of distal radiating portion 144 contacts spacer 198 such that spacer 198 is at least partially compressed and distal radiating portion 144 is at least partially moved proximally relative to trocar 190 and the other components of antenna assembly 120, thus flexing flexible conductive joint 138 and shortening the axial length of the distal portion of antenna assembly 120. In other words, in such embodiments, rather than just flexible conductive joint 138 permitting distal radiating portion 144 to "float," thereby maintaining the target axial distance between trocar 190 and distal radiating portion 144, compressible spacer 198 and flexible conductive joint 138 cooperate to accounting for variation in the components of microwave antenna probe 112 and the engagements therebetween, thus maintaining the target axial distance between trocar 190 and distal radiating portion 144.

Figure 10:
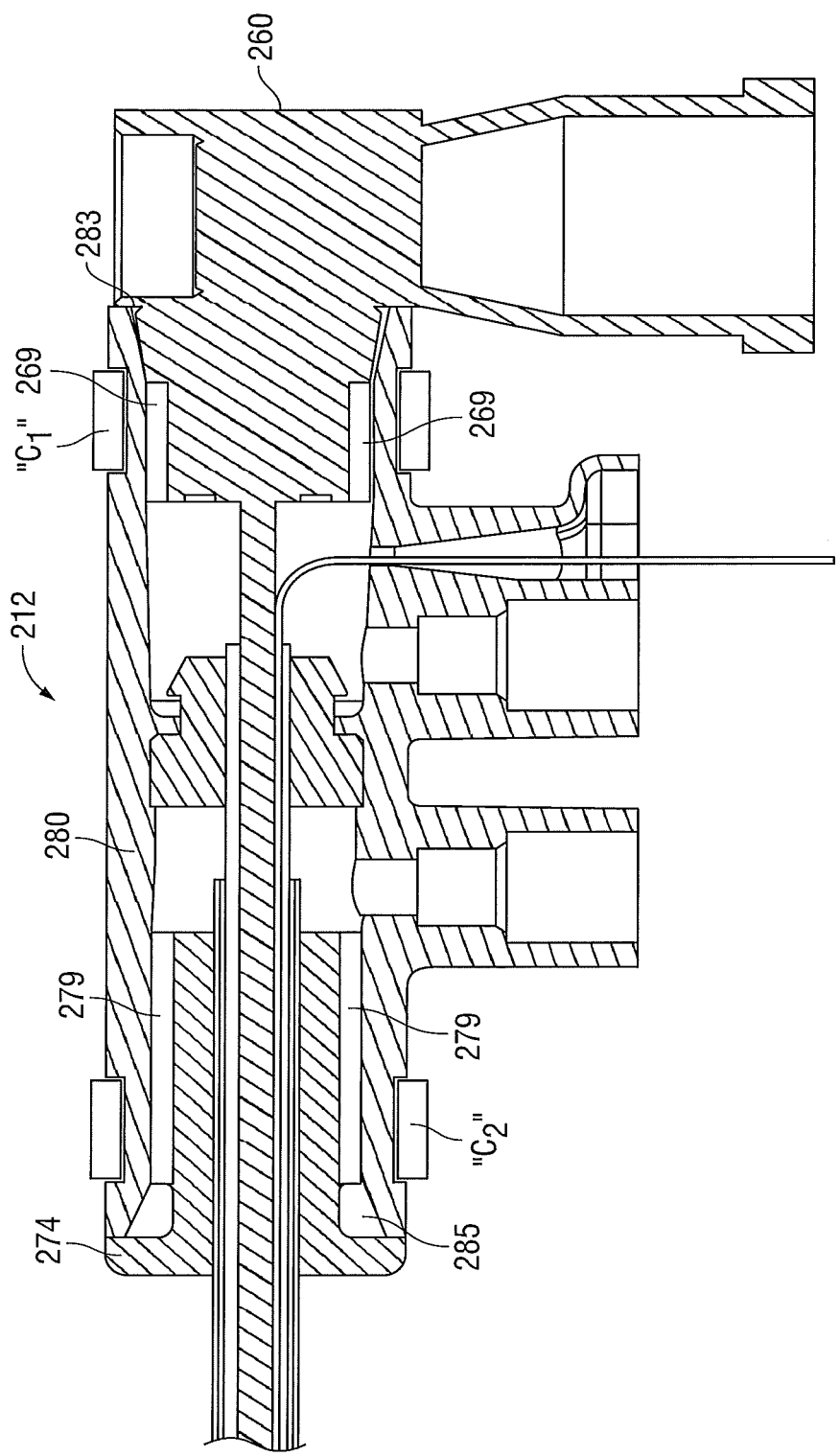
FIG. 10 is a longitudinal, cross-sectional view of a proximal end of another microwave antenna probe provided in accordance with the present disclosure.

Turning now to FIG. 10, another embodiment of a microwave antenna probe provided in accordance with the present disclosure is shown generally identified by reference numeral 212. Microwave antenna probe 212 differs from microwave antenna probe 12 (FIGS. 1-7) in that transition 260 and/or ferrule 274 are sealingly engaged within connection hub 280 via flexible couplings 269, 279, thus permitting at least some degree of axial translation of transition 260 and/or ferrule 274 relative to connection hub 280. Flexible couplings 269, 279 may include a flexible sleeve of material disposed within proximal and distal ports 283, 285, respectively, of connection hub 280 that are configured to receive transition 260 and ferrule 274, respectively, or may define any other suitable configuration that permits axial movement of transition 260 and/or ferrule 274 relative to connection hub 280, while maintaining sealing engagement therebetween.

The above-described flexible couplings 269, 279, between connection hub 280 and transition 260 and/or ferrule 274, respectively, allow for adjustment of the axial distance between the distal end of distal radiating portion 244 (FIG. 11), which is ultimately coupled to transition 260, and the proximal surface of trocar 290 (FIG. 11), which is ultimately coupled to ferrule 274. As such, a target axial spacing between distal radiating portion 244 (FIG. 11) and trocar 290 (FIG. 11) can be achieved by adjusting the relative position of transition 260 and/or ferrule 274 relative to one another and to connection hub 280.

Retaining members, e.g., clips "$C_1$," "$C_2$," O-rings, or other suitable retaining members, may also be provided for engagement about connection hub 280 adjacent proximal and distal ports 283, 285, respectively, to inhibit axial movement of transition 260 and/or ferrule 274 relative to one another and to connection hub 280 once the target axial spacing between distal radiating portion 244 (FIG. 11) and trocar 290 (FIG. 11) has been achieved. More specifically, clips "$C_1$," "$C_2$," sufficiently compress proximal and distal ports 283, 385 of connection hub 280 about transition 260 and ferrule 274, respectively, to retain connection hub 280, transition 260, and ferrule 274 in substantially fixed position relative to one another.

Figure 11:
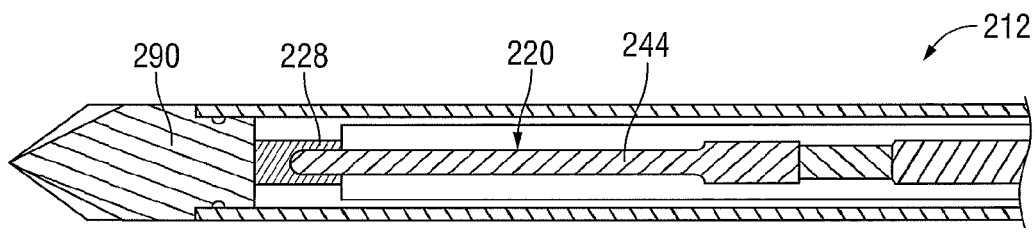
FIG. 11 is a longitudinal, cross-sectional view of a distal end of another microwave antenna probe provided in accordance with the present disclosure.

With reference now to FIG. 11, in conjunction with FIG. 10, antenna assembly 220 may initially include a distal spacer 228 disposed about and extending distally from distal radiating portion 244 of antenna assembly 220. Distal spacer 228 is configured to extend distally from distal radiating portion 244 a distance equal to the target axial distance between distal radiating portion 244 and trocar 290. Further, as will be described in greater detail below, distal spacer 228 may be formed from a dissolvable material.

Antenna assembly 220, including distal spacer 228, is configured for use in conjunction with the flexible couplings 269, 279 between connection hub 280 and transition 260 and/or ferrule 274, respectively, to set and maintain the target axial distance between distal radiating portion 244 and trocar 290. More specifically, upon assembly of microwave antenna probe 212, the distal end distal spacer 228 eventually contacts the proximal surface of trocar 290, thereby urging distal radiating portion 244 proximally and/or trocar 290 distally relative to one another. The proximal urging of distal radiating portion 244 and/or the distal urging of trocar 290 is permitted due to the flexible couplings 269, 279 between connection hub 280 and transition 260 and/or ferrule 274. In other words, upon contact of distal spacer 228 with trocar 290, transition 260 is urged proximally and/or ferrule 274 is urged distally relative to connection hub 280.

With the components of microwave antenna probe 212 fully engaged to one another, and with distal spacer 228 extending from distal radiating portion 244 into contact with trocar 290, the target axial distance between trocar 290 and distal radiating portion 244 is achieved, e.g., since distal spacer 228 extends from distal radiating portion 224 the target axial distance. In embodiments where distal spacer 228 is a permanent component, clips "$C_1$," "$C_2$," are not needed, as distal spacer 228 and the bias of flexible couplings 269, 279 maintains the target axial distance between distal radiating portion 244 and trocar 290.

With respect to other embodiments, once the above-mentioned position has been achieved, clips "$C_1$," "$C_2$" may be engaged about proximal and distal ports 283, 285 of connection hub 280 to retain connection hub 280, transition 260, and ferrule 274 in substantially fixed position relative to one another, thus fixing trocar 290 and distal radiating portion 244 in position defining the target axial distance therebetween. As such, once clips "$C_1$," "$C_2$" are in place, distal spacer 228 is no longer necessary to maintain the target axial distance between trocar 290 and distal radiating portion 244. However, as distal spacer 228 is disposed within microwave antenna probe 212, retrieval of distal spacer 228 may prove difficult. Instead, as mentioned above, distal spacer 228 may be formed from a dissolvable materials such that, once microwave antenna probe 212 is activated and coolant fluid is circulated therethrough into contact distal spacer 228, distal spacer 228 is dissolved, and, thus, is carried out of microwave antenna probe 212 along with the circulating coolant fluid. It is also envisioned that different size spacers 228 be provided for use in accordance with any of the above-described configurations, such that a particular spacer 228 may be selected to achieve a particular axial distance between trocar 290 and distal radiating portion 244, depending on a particular purpose.

Turning now to FIG. 12, another embodiment of a microwave antenna probe provided in accordance with the present disclosure is shown generally identified by reference numeral 312. Microwave antenna probe 312 is similar to microwave antenna probe 212 (FIG. 10), and includes flexible couplings 369, 379 between connection hub 380 and transition 360 and/or ferrule 374, respectively, that allow for adjustment of the axial distance between the distal end of distal radiating portion 344, which is ultimately coupled to transition 360, and the proximal surface of trocar 390, which is ultimately coupled to ferrule 374. Further, the flexible couplings 369, 379 may bias transition 360 and/or ferrule 374 towards a closer-together position, e.g., towards one another. Flexible couplings 369, 379, as mentioned above, allow a target axial spacing between distal radiating portion 344 and trocar 390 to be achieved by adjusting the relative position of transition 360 and/or ferrule 374 relative to one another and to connection hub 380. More specifically, as will be described in greater detail hereinbelow, the relative positions of transition 360 and/or ferrule 374 with respect to each other and connection hub 380 are maintained by sustaining a pre-determined pressure, as applied by coolant fluid, within outer jacket 372 and connection hub 380.

Continuing with reference to FIG. 12, due to the flexible coupling between connection hub 380 and transition 360 and/or ferrule 374, the relative positioning of transition 360 and/or ferrule 374 may be altered by controlling the pressure within connection hub 380, as established by the circulation of coolant fluid flowing through lumen 382 of connection hub 380 and through outer jacket 372. That is, where a relatively greater pressure of coolant fluid is applied, a relatively greater outward force is exerted on transition 360 and ferrule 374 such that transition 360 and ferrule 374 are urged relatively further apart from one another. As a result, the axial distance between trocar 390 and distal radiating portion 344 is relatively greater. On the other hand, where a relatively smaller pressure is applied, a relatively smaller outward force is exerted on transition 360 and ferrule 374 such that transition 360 and ferrule 374 are urged apart a relatively smaller distance (or not at all). In this case, the axial distance between trocar 390 and distal radiating portion 344 is relatively small. In other words, a desired axial spacing between distal radiating portion 344 and trocar 390 may be achieved by establishing a pre-determined pressure within connection hub 380. The particular relationship between the applied pressure and the axial distance may depend on the particular configuration of microwave antenna probe 312, and may be determined experimentally, empirically, or in any other suitable fashion.

In use, when microwave antenna probe 312 is activated, coolant fluid is pumped from fluid source "FS" through tube 317 and into inlet fluid port 387 of connection hub 380 such that the coolant fluid may circulate through lumen 382 of connection hub 380 and through outer jacket 372 to maintain microwave antenna probe 312 in a relatively cooled state during use. Ultimately, the fluid is pumped out of connection hub 380 through outlet fluid port 389, and returns to the fluid source "FS" via tube 319. A pressure sensor "PS" extending into lumen 382 of connection hub 380 and coupled to the fluid source "FS" may also be provided for monitoring the pressure within connection hub 380, although the pressure sensor "PS" may alternatively be independent of the fluid source "FS." The pressure sensor "PS" provides feedback to the fluid source "FS" such that the necessary pressure to maintain transition 360 and ferrule 374 in proper position relative to one another and, thus, to maintain the target axial distance between trocar 390 and distal radiating portion 344 can be readily achieved and maintained.

Figure 13A:
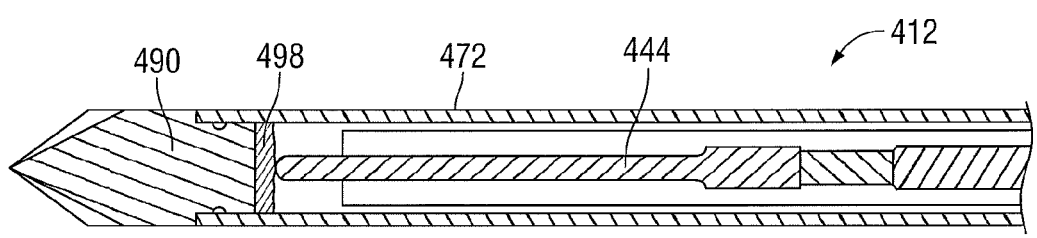
FIG. 13A is a longitudinal, cross-sectional view of a distal end of another microwave antenna probe provided in accordance with the present disclosure, wherein the microwave antenna probe is disposed in an initial condition.
Figure 13B:
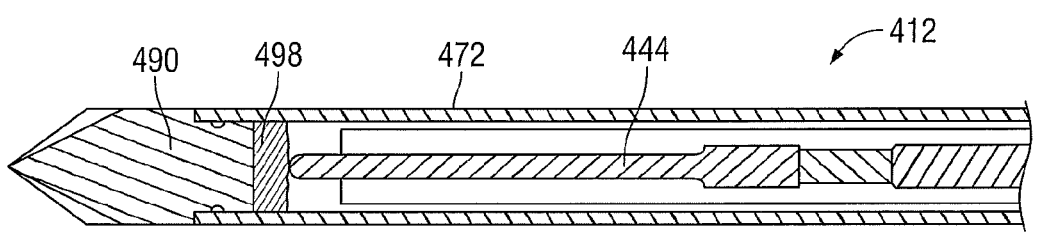
FIG. 13B is a longitudinal, cross-sectional view of the microwave antenna probe of FIG. 13A, wherein the microwave antenna probe is disposed in a so-called "use" condition.

With reference now to FIG. 13A-13B, another embodiment of a microwave antenna probe 412 provided in accordance with the present disclosure is shown including a spacer, or expandable member 498 disposed within outer jacket 472 and positioned on the proximal surface of trocar 490. Spacer, or expandable member 498 may be configured to expand upon contact within coolant fluid, upon heating, or in any suitable manner such that expandable member 498 is expanded from a first, compressed position, as shown in FIG. 13A, to a second, expanded position, as shown in FIG. 13B, when use of microwave antenna probe 412 is initiated. In the expanded position, expandable member 498 is configured to define a thickness equal to the target axial distance between trocar 490 and distal radiating portion 444 and is further configured to urge distal radiating portion 444 proximally relative to trocar 490 upon expansion. As such, in the expanded position of expandable member 498, and, thus, during use of microwave antenna probe 412, the target axial distance between trocar 490 and distal radiating portion 444 is achieved. Expandable member 498 may be used in conjunction with flexible conductive joint 138 (see FIGS. 9A-9B), flexible couplings 269, 279 (FIG. 10), or any other suitable mechanism configured to permit axial movement of distal radiating section 444 relative to trocar 490, e.g., via permitting axial movement of the transition relative to the ferrule, such that, upon urging by expandable member 498 as a result of expansion of expandable member 498, the target axial distance between distal radiating portion 444 and trocar 490 is achieved and maintained throughout use.

Figure 14:
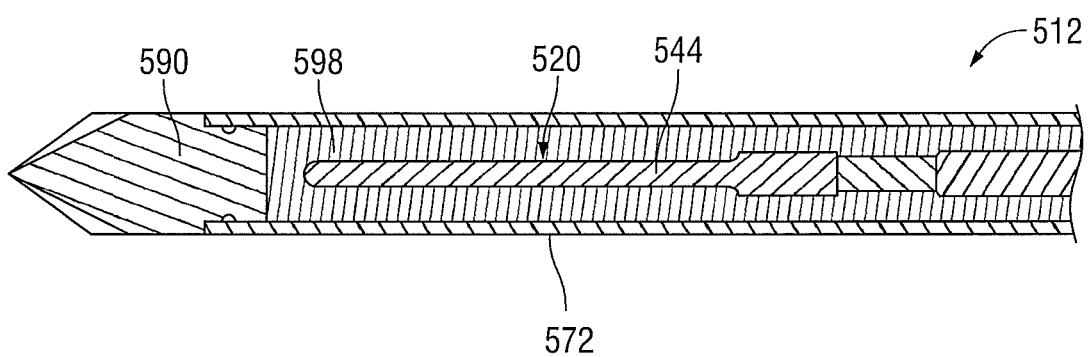
FIG. 14 is a longitudinal, cross-sectional view of a distal end of another microwave antenna probe provided in accordance with the present disclosure.

Turning now to FIG. 14, another embodiment of a microwave antenna probe provided in accordance with the present disclosure and configured to maintain the target axial distance between the distal radiating portion and the trocar during use is shown generally identified by reference numeral 512. Microwave antenna probe 512 is similar to microwave antenna probe 12 (FIGS. 1-7), except that, rather than providing for circulation of coolant fluid through outer jacket 572, antenna assembly 520 is substantially surrounded by a phase-change material 598 initially disposed in a solid state. More specifically, phase-change material 598 is disposed about antenna assembly 520 such that phase-change material 598 extends distally from distal radiating portion 544 a distance equal to the target axial distance between trocar 590 and distal radiating portion 544. Accordingly, during assembly, antenna assembly 520 is inserted into outer jacket 572 (or outer jacket 572 is disposed about antenna assembly 520) such that the distal end of phase-change material 598 abuts the proximal surface of trocar 590, thereby establishing the target axial distance between trocar 590 and distal radiating portion 544. With this target spacing achieved, the remaining components of microwave antenna probe 512 may be fixedly engaged to one another.

With continued reference to FIG. 14, in use, when microwave antenna probe 512 is activated to apply energy to tissue to treat, e.g., ablate, tissue, antenna assembly 520 is heated. As a result, phase-change material 598 is likewise heated. Upon sufficient heating of phase-change material 598, phase-change material 598 is transformed from its initial solid state to a fluid, e.g., liquid, state, whereby heat is absorbed by phase-change material 598. The absorption of heat by the phase-change material 598 helps maintain microwave antenna probe 512 in a relatively cooled state during use. Further, since the components of microwave antenna probe 512 are already assembled and fixedly engaged to one another at this point, the transformation of phase-change material 598 from the solid state to the fluid, e.g., liquid, state does not alter the axial distance between distal radiating portion 544 and trocar 590. Phase-change material 598 may be disposed within a compartmentalized jacket (not explicitly shown) that includes a plurality of pockets, each retaining a portion of phase-change material 598, or may be provided in any other suitable configuration.

Figure 15:
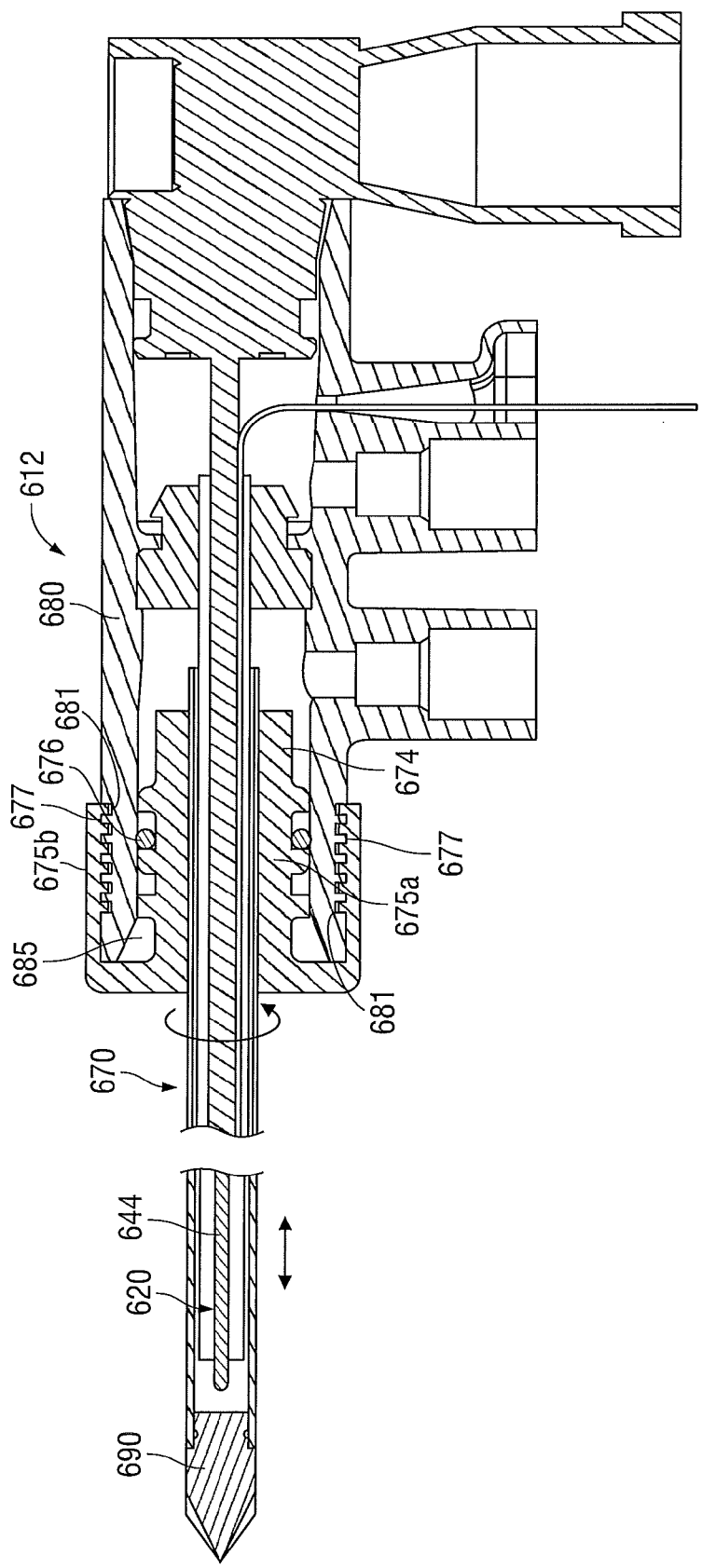
FIG. 15 is a longitudinal, cross-sectional view of another microwave antenna probe provided in accordance with the present disclosure.

With reference now to FIG. 15, another embodiment of a microwave antenna probe provided in accordance with the present disclosure for achieving a target axial distance between the distal radiating portion and the trocar during use is shown generally identified by reference numeral 612. Microwave antenna probe 612 is similar to microwave antenna probe 12 (FIGS. 1-7) except that outer jacket and trocar assembly 670 is axially extendable and retractable relative to antenna assembly 620 to vary the axial distance between distal radiating portion 644 and trocar 690.

Continuing with reference to FIG. 15, ferrule 674 of outer jacket and trocar assembly 670 is rotatably mounted relative to distal port 685 of connection hub 680 such that ferrule 674 may be rotated relative to outer jacket and trocar assembly 670 to extend or retract trocar 690 relative to distal radiating portion 644, while mainlining the sealing engagement between ferrule 674 and connection hub 680 via O-ring 676. More specifically, ferrule 674 includes a base 675a that is configured for insertion into distal port 685 of connection hub 680 for sealing engagement therein via O-ring 676, while annular flange 675b of ferrule 674 is configured for positioning about distal port 685 of connection hub 680 in threading engagement therewith. That is, annular flange 675b of ferrule 674 defines threading 677 on the internal surface thereof that is pitched relative to and configured to engage complementary threading 681 disposed on the outer surface of connection hub 680 adjacent distal port 685. Due to the relative pitch between threadings 677, 681, rotation of ferrule 674 relative to connection hub 680 effects axial translation of ferrule 674 relative to connection hub 680. As such, by rotating ferrule 674 relative to connection hub 680, the relative spacing between trocar 690 and distal radiating portion 644 can be varied such that a target axial distance therebetween can be achieved. Visual markings or indicia (not explicitly shown) may also be provided to allow the user to ascertain the relative position of outer jacket and trocar assembly 670. Further, a locking mechanism (not shown) may be provided to lock outer jacket and trocar assembly 670 in position once the target axial spacing between trocar 690 and distal radiating portion 644 has been achieved.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical probe, comprising:
   a feedline configured to couple to a source of energy
   a connection hub;
   an antenna assembly directly coupled to the connection hub and extending distally from the connection hub, the antenna assembly defining a distal end and including a radiating portion disposed towards the distal end of the antenna assembly, the radiating portion defining a longitudinal axis and configured to deliver energy to tissue to treat tissue;
   an outer jacket directly coupled to the connection hub and extending distally therefrom, the outer jacket enclosing the distal end of the antenna assembly and including a distal end member configured to be spaced-apart from the distal end of the antenna assembly a target axial distance; and
   an electrically conductive flexible member interconnecting the feedline and the radiating portion and configured to move axially along the longitudinal axis to confine relative axial movement between the distal end of the antenna assembly and the distal end member such that the target axial distance between the distal end of the antenna assembly and the distal end member is maintained.

2. The surgical probe according to claim 1, further comprising a spacer interdisposed between the distal end member and the distal end of the antenna assembly and configured to flex the electrically conductive flexible member to maintain the target axial distance between the distal end of the antenna assembly and the distal end member.

3. The surgical probe according to claim 2, wherein the spacer is formed at least partially from a compressible material.

4. The surgical probe according to claim 2, wherein the spacer is formed at least partially from a dissolvable material.

5. The surgical probe according to claim 2, wherein the spacer is formed at least partially from an expandable material.

6. The surgical probe according to claim 1, wherein fluid is configured to be circulated within the connection hub and the outer jacket at a pre-determined pressure to flex the electrically conductive flexible member to maintain the target axial distance between the distal end of the antenna assembly and the distal end member.

7. The surgical probe according to claim 6, further comprising a pressure sensor configured to sense the fluid pressure within the connection hub and the outer jacket.

8. The surgical probe according to claim 1, wherein the antenna assembly includes a transition sealingly coupled to the connection hub via the electrically conductive flexible member such that the antenna assembly is axially movable relative to the connection hub.

9. The surgical probe according to claim 8, further comprising a clip configured for engagement about the connection hub to inhibit axial movement of the antenna assembly relative to the connection hub.

10. The surgical probe according to claim 1, wherein the outer jacket includes a ferrule sealingly coupled to the connection hub via the electrically conductive flexible member such that the outer jacket is axially movable relative to the connection hub.

11. The surgical probe according to claim 10, further comprising a clip configured for engagement about the connection hub to inhibit axial movement of the outer jacket relative to the connection hub.

12. The surgical probe according to claim 1, wherein the distal end member includes a trocar configured to facilitate penetration through tissue.

13. A microwave antenna, comprising:
a feedline configured to couple to a source of energy;
a radiating portion defining a longitudinal axis and configured to deliver energy to tissue;
an outer jacket enclosing the radiating portion and including a distal end member configured to be spaced-apart from the radiating portion a target axial distance; and
an electrically conductive flexible joint interconnecting the feedline and the radiating portion and configured to move axially along the longitudinal axis to prevent relative axial movement between the radiating portion and the distal end member such that the target axial distance between the radiating section and the distal end member is maintained.

14. The microwave antenna according to claim 13, further comprising a connection hub directly coupled to the outer jacket via the joint.

15. The microwave antenna according to claim 13, further comprising a spacer disposed between the distal end member and the radiating portion and configured to engage the radiation portion to compress the electrically conductive flexible joint and move the radiating portion axially along the longitudinal axis.

16. The microwave antenna according to claim 15, wherein the spacer is compressible.

17. A microwave antenna, comprising:
a feedline configured to couple to a source of energy;
a radiating portion defining a longitudinal axis and configured to deliver energy to tissue;
a distal end member configured to be spaced-apart from the radiating portion a target axial distance;
an electrically conductive flexible joint interconnecting the feedline and the radiating portion; and
a spacer disposed between the distal end member and the radiating portion and configured to engage the radiating portion to compress the electrically conductive flexible joint and move the radiating portion axially along the longitudinal axis such that the target axial distance between the radiating portion and the distal end member is maintained.

18. The microwave antenna according to claim 17, wherein the distal end member is disposed on an outer jacket enclosing the radiating portion.

19. The microwave antenna according to claim 17, wherein compression of the electrically conductive flexible joint to move the radiating portion axially along the longitudinal axis is configured to prevent relative axial movement between the radiating portion and the distal end member.

* * * * *

UNITED STATES PATENT AND TRADEMARK OFFICE
CERTIFICATE OF CORRECTION

PATENT NO. : 9,901,398 B2
APPLICATION NO. : 13/908463
DATED : February 27, 2018
INVENTOR(S) : Brannan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 186 days.

Signed and Sealed this
Fifth Day of February, 2019

Andrei Iancu
*Director of the United States Patent and Trademark Office*